US008759317B2

(12) United States Patent
Vesely

(10) Patent No.: US 8,759,317 B2
(45) Date of Patent: Jun. 24, 2014

(54) METHOD OF TREATMENT OF CANCER USING GUANOSINE 3', 5' CYCLIC MONOPHOSPHATE (CYCLIC GMP)

(75) Inventor: David L. Vesely, Tampa, FL (US)

(73) Assignee: University of South Florida, Tampa, FL (US)

( * ) Notice: Subject to any disclaimer, the term of this patent is extended or adjusted under 35 U.S.C. 154(b) by 172 days.

(21) Appl. No.: 11/162,056

(22) Filed: Aug. 26, 2005

(65) Prior Publication Data

US 2006/0014689 A1  Jan. 19, 2006

Related U.S. Application Data

(63) Continuation-in-part of application No. 10/708,688, filed on Mar. 18, 2004, now Pat. No. 6,943,147.

(60) Provisional application No. 60/522,178, filed on Aug. 26, 2004.

(51) Int. Cl.
*A61K 31/708* (2006.01)
*A61K 38/22* (2006.01)
*C07K 14/58* (2006.01)

(52) U.S. Cl.
CPC .............. *A61K 31/708* (2013.01); *A61K 38/22* (2013.01); *C07K 14/58* (2013.01); *Y10S 930/05* (2013.01)
USPC ............................... 514/48; 514/12.4; 930/50

(58) Field of Classification Search
None
See application file for complete search history.

(56) References Cited

U.S. PATENT DOCUMENTS

| | | | | |
|---|---|---|---|---|
| 4,753,945 A * | 6/1988 | Gilbard et al. | ........... | 514/263.31 |
| 5,352,770 A * | 10/1994 | Matsuo | ........... | 530/326 |
| 6,943,147 B2 * | 9/2005 | Vesely | ........... | 514/12 |
| 7,825,092 B2 * | 11/2010 | Vesely | ........... | 514/1.1 |
| 7,846,900 B2 * | 12/2010 | Vesely | ........... | 514/12.4 |
| 8,343,919 B2 * | 1/2013 | Vesely | ........... | 514/12.4 |
| 2002/0094326 A1 * | 7/2002 | Donahue et al. | ........... | 424/93.21 |
| 2003/0105000 A1 * | 6/2003 | Pero et al. | ........... | 514/12 |
| 2003/0215528 A1 * | 11/2003 | Graham et al. | ........... | 424/718 |
| 2004/0258687 A1 * | 12/2004 | Waldman et al. | ........... | 424/143.1 |
| 2005/0209139 A1 * | 9/2005 | Vesely | ........... | 514/12 |
| 2006/0019256 A1 * | 1/2006 | Clarke et al. | ........... | 435/6 |

OTHER PUBLICATIONS

Gura (Science, 1997, 278:1041-1042).*
Kaiser (Science, 2006, 313, 1370).*
Schwede et al. (Pharmacology & Therapeutics, 2000 87:199-226).*
Scott et al (Nature Genetics, 1999, 21:440-443).*
Busken, C et al, (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons : New York, 1981; appendix C).*
Vesely et al. (Euro. J. Clin. Invest. 2005, 35:700-710).*
Freshney (Culture of Animal Cells, A Manual of Basic Technique, Alan R. Liss, Inc., 1983, New York, p. 3-4).*
Dermer (Bio/Technology, 1994, 12:320).*
Zellner et al (Clin. Can. Res., 1998, 4:1797-1802).*
Zips et al (In vivo, 2005, 19:1-7).*
White et al. (Nature, Jan. 1993, 361:263-266).*
Kumar et al. (Biochimica et Biophysica Acta, 1997, 1356:221-228).*
Pitari et al. (Proc. Natl. Acad. Sci. Jul. 3, 2001 96:7846-7851).*
Nguyen et al. (J. Nutrition, 1993 123:259-269).*
ATCC No. CCL-248 (T84, 1984).*
Vesely et al. (Euro. J. Clin. Invest. Jun. 2005, 35: 388-398).*
Tannock, I.F. (Experimental Chemotherapy, Ch. 19—p. 338 and 352-359, in The Basic Science Of Oncology Tannock and Hill, eds., New York 1992).*
Tressler et al. (Int. J. Cancer 1994 57:568-573).*
Vesely et al., Four Peptides Decrease the Number of Human Pancreatic Adenocarcinoma Cells, Eur. J. Clic. Invest., 2003, vol. 33, p. 998-1005.
Vesely et al., Novel Therapeutic Approach for Cancer Using Four Cardiovascular Hormones, Eur. J. Clic. Invest., 2004, vol. 34, p. 674-682.
Vesely et al., Four Peptide Hormones Decrease the Number of Human Breast Adenocarcinoma Cells, Eur. J. Clic. Invest., 2005, vol. 35, p. 60-69.
Vesely et al., Five Cardiovascular Hormones Decrease the Number of Human Small-Cell Lung Cancer Cells, Eur. J. Clic. Invest., 2005, vol. 35, p. 388-398.
Vesely et al., Atrial Natriuretic Peptides in Pathophysiological Disease, Elsevier Science B.V., 2001, vol. 51, p. 647-658.
Linder, M.W. et al. "Pharmacogenetics: a laboratory tool for optimizing therapeutic efficiency" *Clinical Chem.*, 1997, 43(2):254-266.

(Continued)

*Primary Examiner* — Peter J Reddig
(74) *Attorney, Agent, or Firm* — Saliwanchik, Lloyd & Eisenschenk

(57) ABSTRACT

A method of treating cancer through use of guanosine 3',5'-cyclic monophosphate (cyclic GMP). Cyclic GMP decreases the number of human breast cancer and prostate adenocarcinoma as well as small-cell and squamous lung cells in culture by 30% (1 μM), 84% (1 mM), 31% (1 μM), and 30% (1 μM), respectively. Cyclic GMP decreases DNA synthesis in human pancreatic, breast, and prostate adenocarcinomas as well as small-cell and squamous cell carcinomas of the lung at its 1 μM concentration by 51%, 54%, 56%, 50% and 52%, respectively. Cyclic GMP when infused for one week decreases the tumor volume of human pancreatic adenocarcinomas in athymic mice 95% compared to untreated animals with human pancreatic adenocarcinomas.

18 Claims, 8 Drawing Sheets

(56) References Cited

OTHER PUBLICATIONS

Wigle, D.A. et al. "ANP secretion from small cell lung cancer cell lines: a potential model of ANP release" *Am. J. Physiol. Heart. Circ. Physiol.*, 1995, 268:H1869-H1874, abstract only.

Sugimoto, T. et al. "Atrial natriuretic peptide induces the expression of MKP-1, a mitogen-activated protein kinase phosphatase, in glomerular mesangial cells" *J. Biol. Chem.*, 1996, 271(1):544-547.

Haneda, M. et al. "Differential inhibition of mesangial MAP kinase cascade by cyclic nucleotides" *Kidney Int'l.*, 1996, 50:384-391.

* cited by examiner

Fig. 8

|  | Volume[B] (mm$^3$) | Increase[C] |
|---|---|---|
| Baseline[A] | 1.8 | — |
| 1st week | 35.3 | 20-fold |
| 2nd week | 124 | 69-fold |
| 3rd week | 309 | 172-fold |
| 4th week | 539 | 299-fold |
| 5th week | 1003 | 557-fold |
| 6th week | 1307 | 726-fold |
| 7th week | 1783 | 991-fold |
| 8th week | 2351 | 1306-fold |

METHOD OF TREATMENT OF CANCER USING GUANOSINE 3', 5' CYCLIC MONOPHOSPHATE (CYCLIC GMP)

CROSS REFERENCE TO RELATED APPLICATIONS

This application claims priority to U.S. Provisional Patent Application 60/522,178, entitled "Therapeutic Approach for Treating Cancer Using Cardiovascular Hormones," filed Aug. 26, 2004; and is a Continuation-in-Part of U.S. patent application Ser. No. 10/708,688 entitled, "Cancer Treatment Using proANP Peptides," filed Mar. 18, 2004, now U.S. Pat. No. 6,943,147, the texts of which are incorporated herein by reference.

BACKGROUND OF THE INVENTION

Human pancreatic adenocarcinomas have the lowest 5-year survival rate of all common cancers. The five-year survival rate of persons with adenocarcinoma of the pancreas is 1%. The median survival is 4.1 months. Current cancer chemotherapy and surgery prolong survival by a few months but the above survival rates are for persons treated with surgery and/or currently available cancer chemotherapeutic agents.

A family of peptides referred to as atrial natriuretic peptides (ANPs) are synthesized within the heart and stored in the atrial myocyte as prohormones for rapid release in response to stimuli. The atrial natriuretic peptide (ANP) gene synthesizes a 126 amino acid (a.a.) prohormone which contains four peptide hormones consisting of a.a. 1-30 (i.e., long acting natriuretic peptide, LANP) a.a. 31-67 (vessel dilator), a.a. 79-98 (kaliuretic peptide) and atrial natriuretic peptide (ANP, a.a, 99-126 of this prohormone). Known biologic properties of these four peptide hormones include blood pressure lowering, diuresis, enhanced sodium and/or potassium excretion when infused into healthy animals and humans. One of these peptide hormones, i.e., ANP has been investigated for growth regulatory properties. In blood vessels, ANP inhibits smooth muscle cell proliferation (hyperplasia) as well as smooth muscle cell growth (hypertrophy). ANP has growth-regulatory properties in a variety of other tissues including brain, bone, myocytes, red blood cell precursors, and endothelial cells. In the kidney, ANP causes antimitogenic and antiproliferative effects in glomerular mesangial cells via inhibiting DNA synthesis. [Cyclic GMP] mediates most of the effects of these four peptide hormones. Thus, cyclic GMP causes vasodilation by itself and mediates the blood pressure lowering effects of these hormones. Vessel dilator and LANP as well as ANP enhance membrane-bound guanylate cyclase to increase cyclic GMP in vasculature. Cyclic GMP [i.e., 8-bromoguanosine 3',5'-cyclic monophosphate] decreases the number of human breast and prostate adenocarcinomas, as well as small-cell and squamous cell lung carcinoma cells in culture by 30% (1 µM), 84% (1 mM), 31% (1 µM) and 30% (1 µM).

SUMMARY OF INVENTION 8-bromo-cyclic GMP (1 µM) decreases DNA synthesis in human pancreatic, breast, and prostate adenocarcinoma cells as well as human small-cell and squamous cell lung carcinoma cells by 51%, 54%, 56%, 50%, and 52%, respectively. Dose-response curves on human pancreatic cancer cells revealed that 8-bromo-cyclic GMP decreased DNA synthesis in these cancer cells by 46%, 42%, 39% and 34% (all P<0.05) at its 3 mM, 1 mM, 100 µM, and 1 µM concentrations respectively. Even at a 1 nM (i.e., $10^{-9}$ M) of 8-bromo-cyclic GMP there was a 25% inhibition of DNA synthesis in the human pancreatic adenocarcinoma cells. At 100 µM of 8-bromo-cyclic GMP, its effects on DNA synthesis in the pancreatic adenocarcinoma cells became not significant (14% decrease). Cell cycle analysis performed by Becton Dickinson flow cytometer FACS scan indicates that cyclic GMP decreases the number of breast cancer cells in the S-phase of the cell cycle by 39% (i.e., causing cell cycle arrest). 8-bromo-cyclic GMP when infused for two weeks at 2.4 µg/kg body weight/min decreased the tumor volume of human pancreatic adenocarcinomas in athymic mice in one week by 95% compared to untreated human pancreatic tumors in athymic mice.

In one embodiment, the present invention provides a method of modulating the growth of cancer cells comprising the step of contacting at least one target cell with an effective amount of at least one intracellular mediator of a peptide hormone derived from the atrial natriuretic peptide prohormone. The peptide hormone derived from the atrial natriuretic peptide prohormone is selected from the group consisting of atrial natriuretic peptide, long acting natriuretic peptide, vessel dilator, and kaliuretic peptide. The intracellular mediator of a peptide hormone derived from the atrial natriuretic peptide prohormone is cyclic GMP, or a cell permeable analog thereof. It has been shown that the method provided is effective against adenocarcinomas, sarcomas, small-cell carcinomas and squamous cell carcinoma in vivo.

In an alternate embodiment, the present invention provides a method of inhibiting the growth of cancer cells comprising the steps of contacting at least one target cell with an effective amount of at least one intracellular mediator of a peptide hormone derived from the atrial natriuretic peptide prohormone and co-administering an effective amount of at least one peptide hormone derived from the atrial natriuretic peptide prohormone. As with the previous embodiment, the peptide hormone derived from the atrial natriuretic peptide prohormone is selected from the group consisting of atrial natriuretic peptide, long acting natriuretic peptide, vessel dilator, and kaliuretic peptide and the intracellular mediator is cyclic GMP, or a cell permeable analog thereof.

BRIEF DESCRIPTION OF THE DRAWINGS

For a fuller understanding of the nature and objects of the invention, reference should be made to the following detailed description, taken in connection with the accompanying drawings, in which:

FIG. 8 Mean tumor volume and fold-increase in tumor volume of human pancreatic adenocarcinomas in 30 athymic mice over a two-month period.

DETAILED DESCRIPTION OF THE PREFERRED EMBODIMENT

Figure 1:
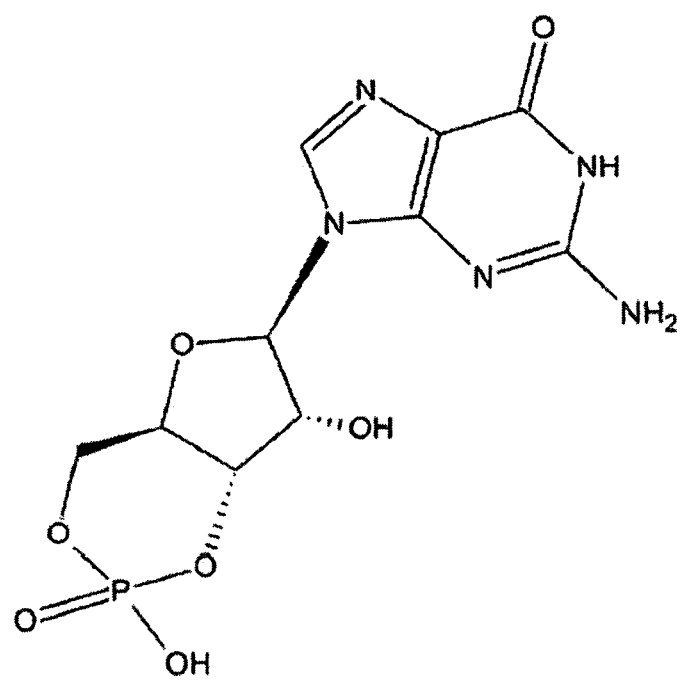
FIG. 1 is a visualization of the cyclic GMP molecule.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Pharmaceutical Compositions

The compounds of the present invention (referred to herein as "active compounds") can be incorporated into pharmaceutical compositions suitable for administration. Such compositions typically comprise a cyclic nucleotide of 3',5'-guanosine monophosphate (cGMP), or a cell permeable analog thereof, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Pharmacogenomics

Agents, or modulators which have a stimulatory or inhibitory effect on cGMP activity as identified by a screening assay can be administered to individuals to treat (prophylactically or therapeutically) disorders (e.g., drug-resistance) associated with aberrant cGMP activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target gene genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

Thus, the activity of cGMP, expression of cGMP, or mutation content of the target gene genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a the target gene modulator, such as a modulator identified by one of the exemplary screening assays described herein.

Terms

As used herein "cyclic GMP," "cGMP," and "cyclic guanosine 3',5-monophosphate" refers to a cyclic nucleotide of guanosine monophosphate which functions at the cellular level to mediate the action of certain hormones across the cellular membrane. [c]GMP is a cylic nucleotide derived from the guanosine triphosphate (GTP). [c]GMP functions a second messenger by activating intracellular protein kinases in response to the binding of membrane-impermeable peptide hormones to the cell surface. [c]GMP is graphically depicted in FIG. 1

As used herein an "analog" of a cyclic GMP refers to a compound which retains chemical structures of cyclic GMP necessary for functional activity of cyclic GMP yet which also contains certain chemical structures which differ from cyclic GMP. An example of an analogue of a naturally-occurring peptide is a peptide which includes one or more non-naturally-occurring amino acids.

As used herein, "a clinical response" is the response of the tumor to treatment with the active compounds of the present invention. Criteria for determining a response to therapy are widely accepted and enable comparisons of the efficacy alternative treatments (see Slapak and Kufe, Principles of Cancer Therapy, in Harrisons 's Principles of Internal Medicine, 13th

edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more tumors. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

The term "modulating" as used herein means changing, adjusting, or varying a property of a tissue, cell, or molecule, cellular proliferative disease or tumor including varying the quantity, activity, size, rate of growth, or capacity of the cellular proliferative disease, tumor, tissue, cell, or molecule. For example, modulation may cause an increase or a decrease in cellular activity, growth, inhibited DNA synthesis, apoptosis or any other biological, functional or immunological properties associated with cGMP.

A "therapeutically effective amount" of the active compounds containing cGMP, atrial natriuretic peptides, or any combination thereof is that amount necessary to provide a clinical response in vivo. The amount of the active compounds containing cGMP, atrial natriuretic peptides, or any combination thereof must be effective to achieve a response, including but not limited to total prevention of (e.g., protection against) and to improved survival rate or more rapid recovery, or improvement or elimination of symptoms associated with a cellular proliferative disease or other indicators as are selected as appropriate measures by those skilled in the art.

Atrial Natriuretic Peptide

Figure 2:
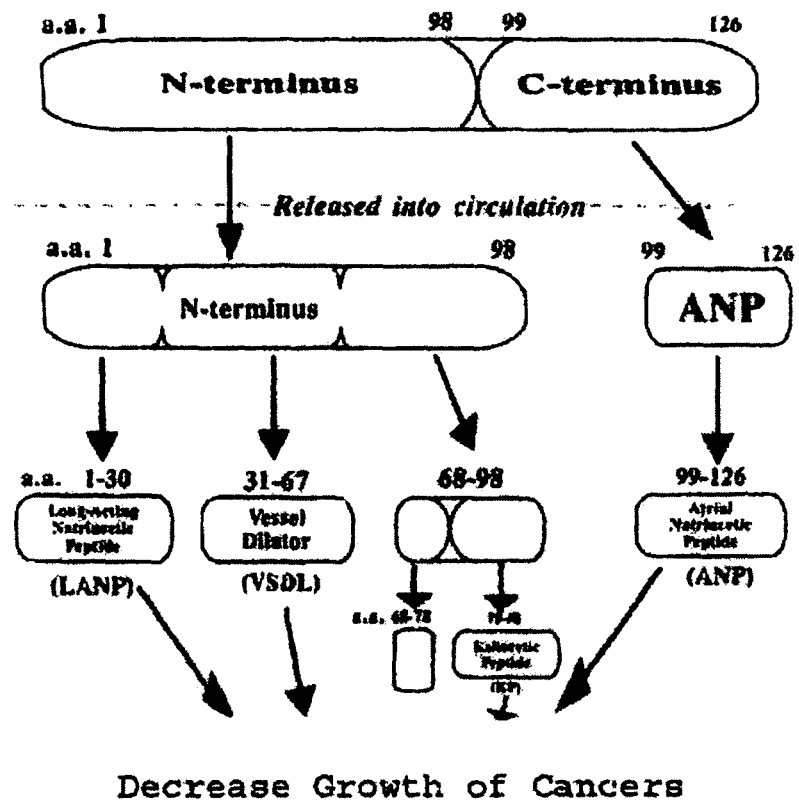
FIG. 2 The atrial natriuretic peptide (ANP) gene synthesizes a 126 amino acid (a.a.) prohormone which contains four peptide hormones consisting of amino acids 1-30 (i.e., long acting natriuretic peptide, LANP) a.a. 31-67 (vessel dilator), a.a. 79-98 (kaliuretic peptide) and atrial natriuretic peptide (ANP, a.a. 99-126 of this prohormone).

The atrial natriuretic peptide (ANP) gene synthesizes four cardiovascular hormones i.e. vessel dilator, long acting natriuretic peptide, kaliuretic peptide and ANP which decrease the number of human pancreatic adenocarcinoma cells in culture by 65%, 47%, 37%, and 34%, respectively. The ANP gene synthesizes a 126 amino acid (a.a.) prohormone which contains four peptide hormones consisting of a.a. 1-30 (i.e., long acting natriuretic peptide, LANP) a.a. 31-67 (vessel dilator), a.a. 79-98 (kaliuretic peptide) and atrial natriuretic peptide (ANP, a.a, 99-126 of this prohormone) (FIG. 2) Previously, none of the cardiovascular hormones have been investigated to determine if they inhibit the growth in vivo. These four hormones were evaluated for their ability to inhibit the growth of human pancreatic adenocarcinomas in athymic mice.

Vessel dilator infused for 14 days completely stopped the growth of human pancreatic adenocarcinomas in athymic mice (n=14) with a decrease in their tumor volume while placebo (n=30) treated mice's tumor volume increased 69-fold (P<O.OO1). When these peptide hormones were infused for four weeks, tumor volume decreased after one week 49%, 28%, and 11% secondary to vessel dilator, long acting natriuretic peptide and kaliuretic peptide with a one— and 20-fold increase in the tumor volume in ANP—and placebo-treated mice. Cyclic GMP inhibited after one week the growth of this cancer 95%. From the second week onwards, the treated cancers began to approximately double their volume weekly.

Accordingly, these results suggest that these peptide hormones have useful anti-cancer properties as they each inhibit the growth of human pancreatic adenocarcinomas in vivo and three decrease the volume of the tumors (up to 49%). Their mechanism of doing so appears to be mediated by cyclic GMP. Cyclic GMP itself inhibited the growth of this cancer 95%. When two of these peptide hormones (i.e., LANP and vessel dilator) were given weekly for four weeks (i.e., pumps with fresh peptide were changed weekly) in a preliminary investigation in athymic mice with human breast carcinomas, after three weeks of treatment the breast adenocarcinoma completely disappeared in the majority of the treated mice. The present in vivo investigations indicate that ideally they should be given weekly.

The inventor has recently found that vessel dilator, long acting natriuretic peptide, kaliuretic peptide and ANP decrease the number of human pancreatic adenocarcinoma cells in culture by 65%, 47%, 37% and 34%, respectively, within 24 hours. This decrease was sustained without any proliferation of the adenocarcinoma cells occurring in the three days following this decrease in number. ANP has also been reported to decrease the number of hepatoblastoma cells in culture. The mechanism of these peptide hormones' decrease in cancer cell number and antiproliferative effects was an 83% or greater inhibition of DNA synthesis but not owing to enhanced apoptosis, i.e., programmed cell death. One of the known mediators of these peptide hormones' mechanism(s) of action, i.e., cyclic GMP inhibited DNA synthesis in these adenocarcinoma cells by 51%. There was no cytotoxicity to normal cells in these studies. None of the cardiovascular hormones have ever been investigated as to whether they could inhibit the growth of adenocarcinomas (or any other cancer) in vivo.

The inventor sought to determine if one or more of the above four cardiovascular hormones could inhibit the growth of human pancreatic adenocarcinomas in vivo in athymic mice by infusing these peptide hormones for two and four weeks. When each of the four peptide hormones inhibited the growth of the human adenocarcinomas in vivo, one of the mechanisms of their action i.e., the intracellular messenger cyclic GMP was investigated as whether it mediates their ability to inhibit the growth of adenocarcinomas in vivo. This novel approach of using cardiovascular hormones and/or cyclic GMP to inhibit the growth of cancers without the usual side effects of currently utilized chemotherapeutic agents (marrow suppression, etc.) with these normally circulating hormones and normal intracellular messenger cyclic GMP is a valuable addition to current treatment of cancer.

EXAMPLE 1

Human Pancreatic Adenocarcinoma Cells

A cell line (ATCC number CRL-2119) of human pancreatic adenocarcinoma cells was purchased from the American Type Culture Association (ATCC), Manassas, Va. This pancreatic adenocarcinoma cell line was derived in 1994 from a nude mouse xenograft of a primary tumor removed from the head of the pancreas. These adenocarcinoma cells are tumorgenic in that they form tumors in athymic nude mice at the site of inoculation that are histologically similar to the tumor of origin.

Culture of Pancreatic Adenocarcinoma Cells for Tumor Formation In Vivo

Propagation of these cells was in Dulbecco's modified Eagle's plus Ham's F12-A 1:1 mixture of Dulbecco's modified Eagle's medium Ham's F12 medium containing 1-2 g $L^{-1}$ of sodium bicarbonate (Sigma Chemical Co., St. Louis, Mo.) supplemented with 15 mM of HEPES and FBS 10%, at a temperature of 37° C., as recommended by the ATCC. Cells were dispensed into new flasks with subculturing every 6-8 days. The growth medium was changed every three days. Prior to injection of these individual cells into animals to produce tumors, the cells were harvested by brief treatment with 0.5% trypsin and 0.02% EDTA followed by fresh medium containing 10% fetal bovine serum to stop trypsinsinization. Only single cell suspension with a viability of >90% were used for the injections.

Animal Model

Homozygous (nu/nu) athymic nude mice from the National Cancer Institute (NCI) were used for these studies. The nude gene in homozygous (nu/nu) mice causes the lack of fur and an abnormal thymus. The deficiency in T-cell function allows athymic mice to accept and grow xenografts as well as allograft of normal and malignant tissues. NCr-nu breeder stock was obtained from the NCI in 1993 after several years of random breeding. It was hysterectomy derived to achieve germfree status prior to its introduction into IBU colonies. This outbred stock has both BALB/c inbred and NIH(S) outbred stock in its genetic background. Six week old athymic mice were utilized for these studies as they weigh approximately 20 grams at this time period, and the osmotic pumps that were used to infuse the respective four cardiovascular hormones and 8-bromo cGMP (cell permeable analog of cyclic GMP) were designed for 20 gram mice.

Human Pancreatic Adenocarcinomas in the Athymic Mice

Mice (20 grams) were given subcutaneous injections of either $1\times10^6$ of normal pancreatic cells (control for injections) or $1\times10^6$ of human pancreatic adenocarcinoma cells in 250 μl of phosphate buffered saline, pH 7.4 on the back of the mice. These mice were palpitated at the site of injection daily starting the seventh day after the injection to determine the latency of the respective tumor formation(s). Tumor growth was followed by electronic digital Vernier caliper measurement every day with tumor volume recorded daily. Tumor volume was calculated by the formula $V=(a\times b2)/2$ where a=largest superficial diameter and b=the smallest superficial diameter.

Research Protocol

When the injected adenocarcinoma cells coalesced into well-defined tumors of at least 1 mm×1 mm (volume=0.5 $mm^3$) or in a series of experiments when the tumors became quite large (volume=118 $mm^3$), osmotic pumps (Alzet Models 1002 and 2004, Duret Corporation, Cupertino, Calif.) containing either 0.9% saline (control infusion) or one of the respective hormones in 0.9% saline as previously described from our laboratory were implanted subcutaneously under anesthesia in the upper back of the athymic mice. All of the peptide hormones for these experiments were synthesized by Phoenix Pharmaceuticals Inc., Belmont, Calif. In the series of experiments where the human pancreatic cancers were allowed to reach a large volume before the pumps in this protocol were implanted, this protocol was to simulate the human situation where these tumors are usually advanced in development and large when first discovered. The Alzet Model 1002 osmotic pump for mice delivers all of its contents (100 μL) over 14 days at a rate of 0.25 μl/h and then stops pumping. The Alzet Model 2004 for mice delivers all of its contents (200 μl) over 28 days at a rate of 0.25 μl/h and then stops pumping. Dose-response curves with 70 ng, 139 ng, and 1.4 μg/kg body weight/min were performed. (These concentrations in 20 gram mice are 1.7 ng, 2.8 ng and 28 ng/min). All mice had free access to water and standard mouse chow (Harland, Teklad, Madison, Wis.). All animals were euthanized one week after completing the respective infusions.

Infusion of Cyclic GMP

The cell permeable analog of cyclic GMP (i.e., 8-bromo cGMP, Sigma-Aldrich, St. Louis, Mo.) was infused via the Alzet Model 1002 osmotic pump (Duret Corp., Cupertino, Calif.) for a two-week period. The concentration utilized for these experiments was 5 mM/min/kg of body weight. 5 mM was chosen as it is the concentration which causes biological effects and is the concentration that was demonstrated in vitro to have maximal effect on inhibiting DNA synthesis in human pancreatic adenocarcinoma cells.

Statistical Analysis

The data obtained in these studies are given as the mean±SEM. Data were evaluated using an ANOVA with a repeated-measures design for within-group comparisons with Fisher's LSD as a post hoc test and a two-factor ANOVA design for between group comparisons. In all cases, P<0.05 was considered the criterion for statistical significance.

Aggressive Growth of Human Pancreatic Adenocarcinomas in Athymic Mice

After injecting the human pancreatic adenocarcinoma cells into athymic mice, in approximately 7 to 14 days these cancer cells develop a well-defined palpable cancer (approximately 1 mm×1 mm; volume=0.5 $mm^3$). This cancer rapidly doubles in tumor volume approximately every two days at first. After one week, the cancers in 30 athymic mice averaged a volume of 35 $mm^3$ (Increase P<0.05 versus baseline) while at the end of two weeks, their volume was 124 $mm^3$ (P<0.001 versus volume of tumors one week previously and versus their volume at baseline). Two weeks after the tumors were first palpable; they had grown 69-fold (FIG. 8). To determine how aggressively this human pancreatic adenocarcinoma grows in athymic mice, 30 untreated mice had tumor volume measured daily for eight weeks. The tumor volume increased 172-fold in three weeks and was almost 300-fold increased four weeks after the tumor first became palpable (FIG. 8). After two months, the volume of the adenocarcinomas was 1306-fold greater than when the tumors first became palpable (FIG. 8).

Vessel Dilator Completely Stops Growth of Large Volume Adenocarcinomas In Vivo

Figure 3:
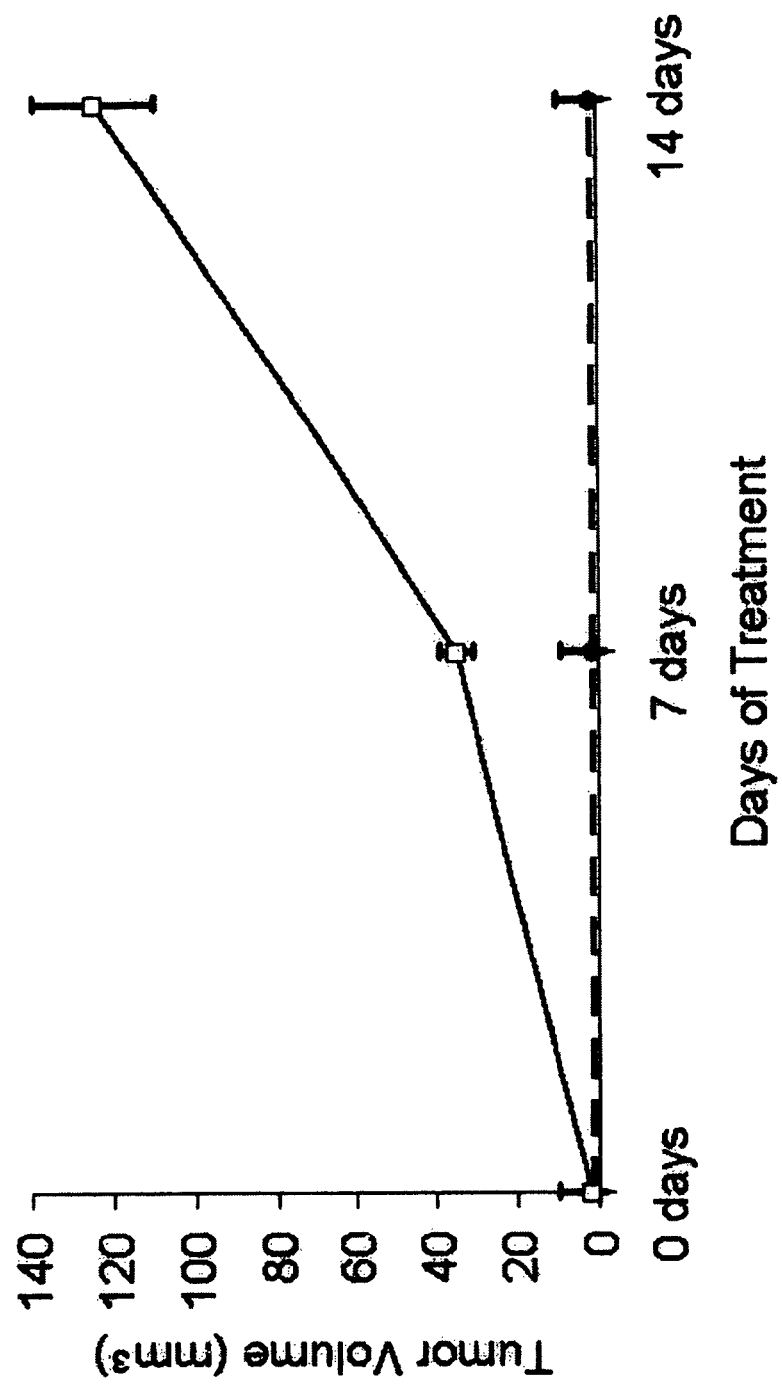
FIG. 3 Vessel dilator (•) completely inhibits the growth of human pancreatic adenocarcinomas in athymic mice. Vessel dilator infused at a concentration of 139 ng/min/kg of body weight (n=14) significantly (P<0.0001) inhibited the growth of pancreatic adenocarcinomas during the two weeks of its infusion compared to placebo (□) treated mice (n=30) when evaluated by a two-factor ANOVA.

In the first series of experiments with the cardiovascular peptide hormones, the adenocarcinomas were allowed to grow to a large volume before the experimental protocol was begun to mimic what occurs in humans, i.e., the pancreatic adenocarcinoma in humans are usually large before they are discovered. Thus, these tumors were allowed to consolidate to 8 mm×5.4 mm, volume=118 $mm^3$ average, before the peptide hormone infusions began. Vessel dilator when infused for 14 days via the subcutaneous osmotic infusion pump at a concentration of 139 ng/min/kg of body weight stopped all growth of the human adenocarcinomas (and decreased their tumor volume by 8%, n=14; P<0.0001 compared to untreated animals; FIG. 3). At the same time in animals given a saline infusion, the adenocarcinomas continued to grow with a 20-fold increase in tumor volume in the first week and their tumor volume was 69-fold greater at the end of the second week. (The adenocarcinomas grew at a similar rate in the saline-infused athymic mice as in another control group of athymic mice who did not have any infusion). During the two weeks of the vessel dilator infusion, the inhibition of growth of the adenocarcinomas (no increase in volume) was significant at P<0.001 when compared to the placebo (saline) treated adenocarcinomas whose volume increased 69-fold (FIG. 3).

No Side Effects or Cytoxicity to Normal Tissues

When the vessel dilator infusion ceased, the human adenocarcinomas began to grow (e.g., increase in tumor volume) again. There was no evidence of cytoxicity to any of the normal tissues during the infusion of vessel dilator. The animals were energetic, healthy appearing and gained weight at a rate comparable to healthy animals. Dose-response studies revealed that at concentrations as low as 1.7 ng/min/20 gram mouse that vessel dilator could completely stop the growth of the human pancreatic adenocarcinomas but at this concentration there was not any decrease in the volume of the tumor by vessel dilator. These experiments demonstrate that vessel dilator can completely inhibit the growth of an aggressively growing cancer, even when the cancer has a very large volume when first treated.

Figure 4:
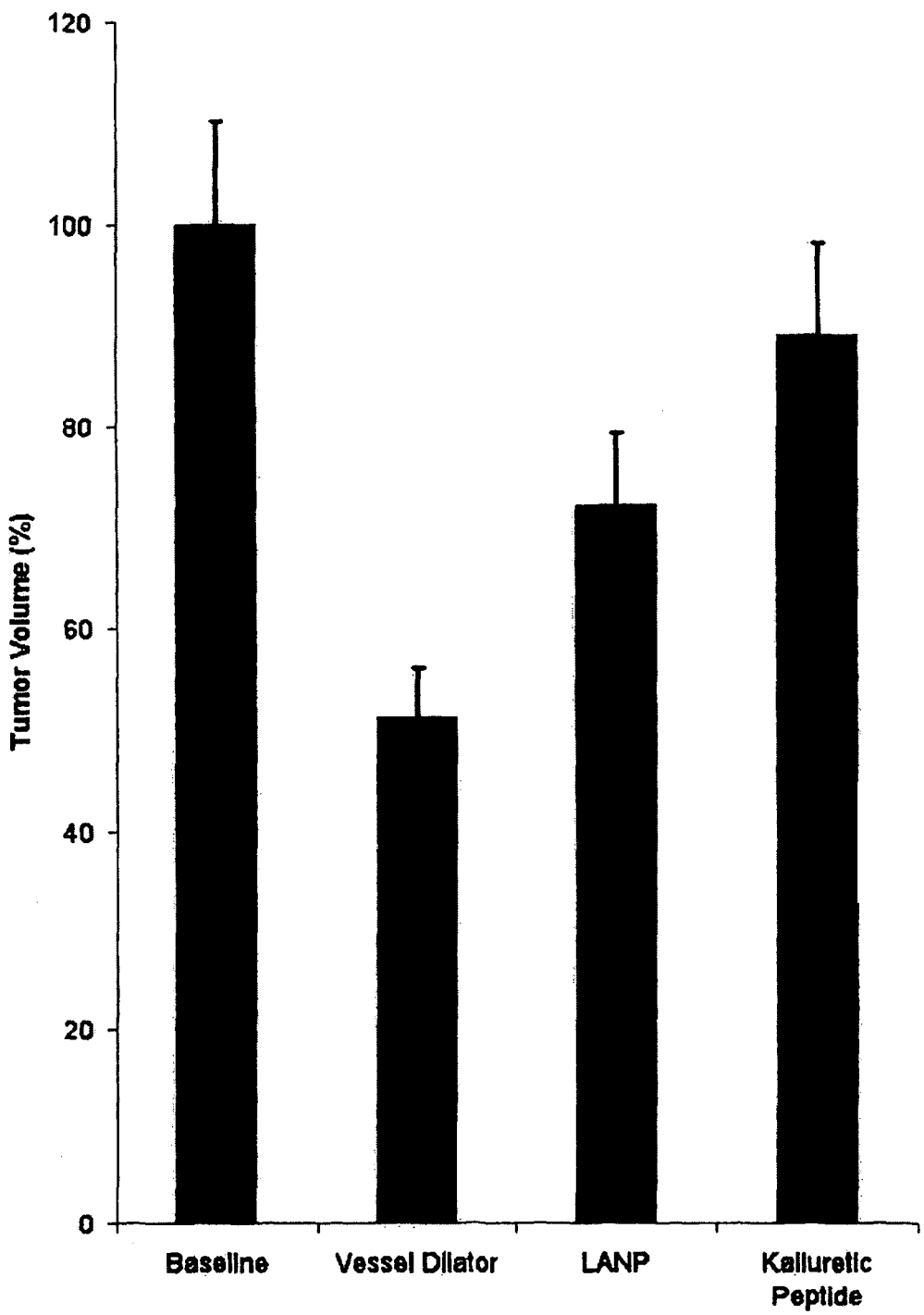
FIG. 4 Long acting natriuretic peptide (LANP), vessel dilator, and kaliuretic peptide decrease tumor volume during the first week of treatment with 1.4 µg/kg body wt/min. compared to their baseline tumor volume, i.e., palpable tumor volume before infusion, this decrease in tumor volume was significant at P<0.01 for vessel dilator and P<0.05 for long acting natriuretic peptide and kaliuretic peptide when evaluated by ANOVA with repeated measures design with a Fishers LSD as a post hoc test. This decrease in tumor volume versus control (20-fold increase) was significant at P<0.001 for each of these peptide hormones. (n=5 in each group).
Figure 5:
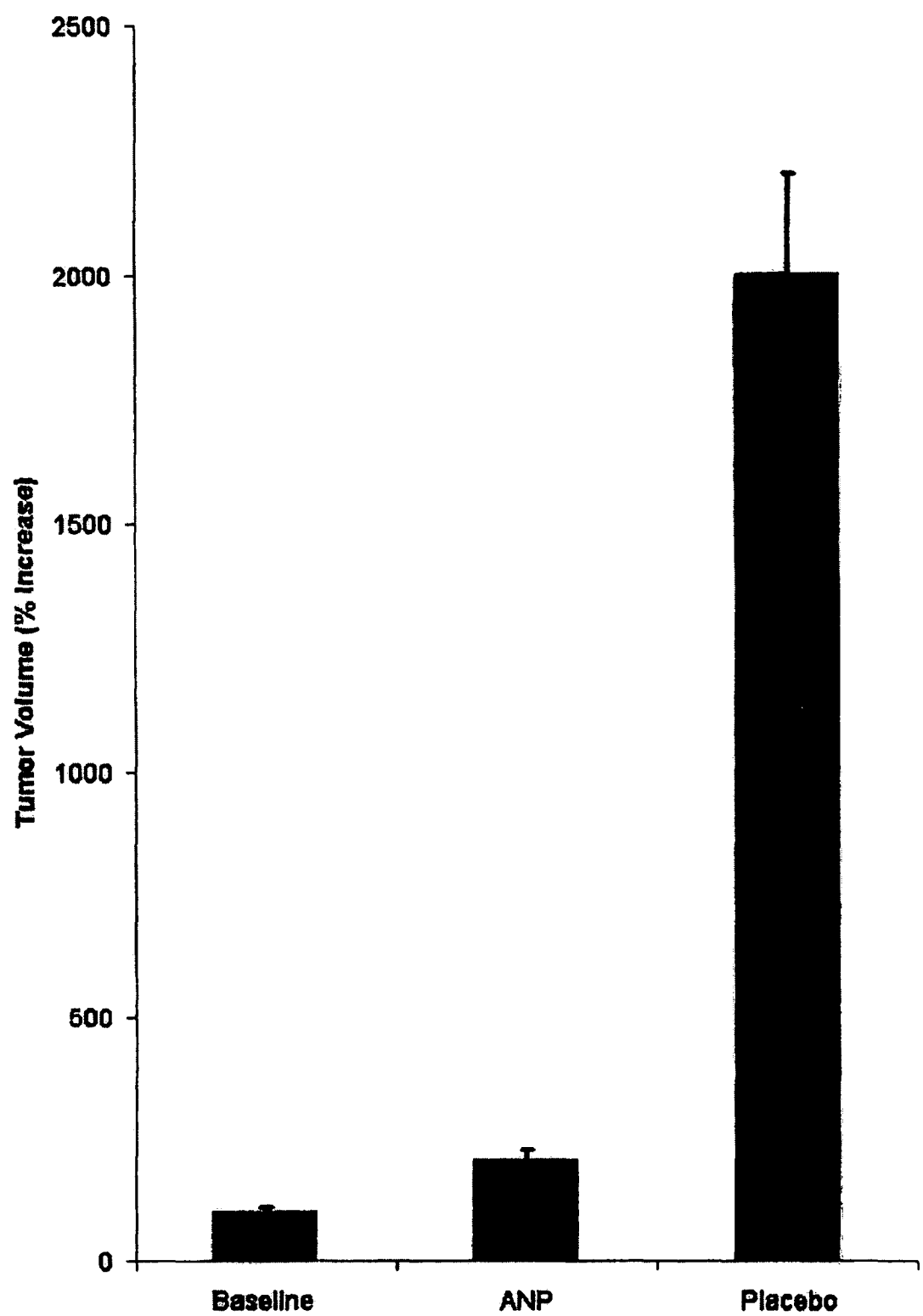
FIG. 5 Atrial natriuretic peptide (ANP) decreases the growth of human pancreatic adenocarcinomas. During the first week of its infusion, ANP at 1.4 µg/kg of body weight/min decreased the growth of the pancreatic adenocarcinomas from 20-fold increase for the placebo-treated adenocarcinoma (n=30) to a 2-fold (n=5) increase compared to its baseline (first palpable) tumor volume which was significant at P<0.001 when evaluated with a 2-factor ANOVA for between group comparisons.

Four Peptide Hormones Inhibit Growth of Human Adenocarcinomas with Decrease in Tumor Volume Secondary to Three of the Cardiovascular Hormones After this information was obtained, the second group of experiments were designed to answer the question whether one or more of the four peptide hormones could decrease the size of the human adenocarcinomas growing in the athymic mice if a larger dose (i.e., 10-fold increase) of the respective peptide hormones was given for a longer period of time (i.e., one month) to adenocarcinomas that were smaller when treatment with the respective peptide hormones began. After one week of vessel dilator at 1.4 µg/kg body weight/min (i.e., 28 ng/min/per 20 gram mouse), the human adenocarcinomas decreased their tumor volume by 49% ($P<0.01$) (FIG. 4). Long acting natriuretic peptide at the same concentration decreased the tumor volume of the adenocarcinomas by 28% ($P<0.05$) (FIG. 4). Kaliuretic peptide, at the same concentration, decreased the tumor volume of the adenocarcinomas by 11% ($P<0.05$) after the first week of its infusion (FIG. 4). Thus, these three peptide hormones not only stopped the growth of the cancers but also decreased the cancer's tumor volume. Atrial natriuretic peptide (ANP) slowed the growth of the adenocarcinomas with the tumor volume increasing 109% compared to a 2000%-fold increase in tumor volume in placebo-treated animals during the same time period (FIG. 5).

Figure 6:
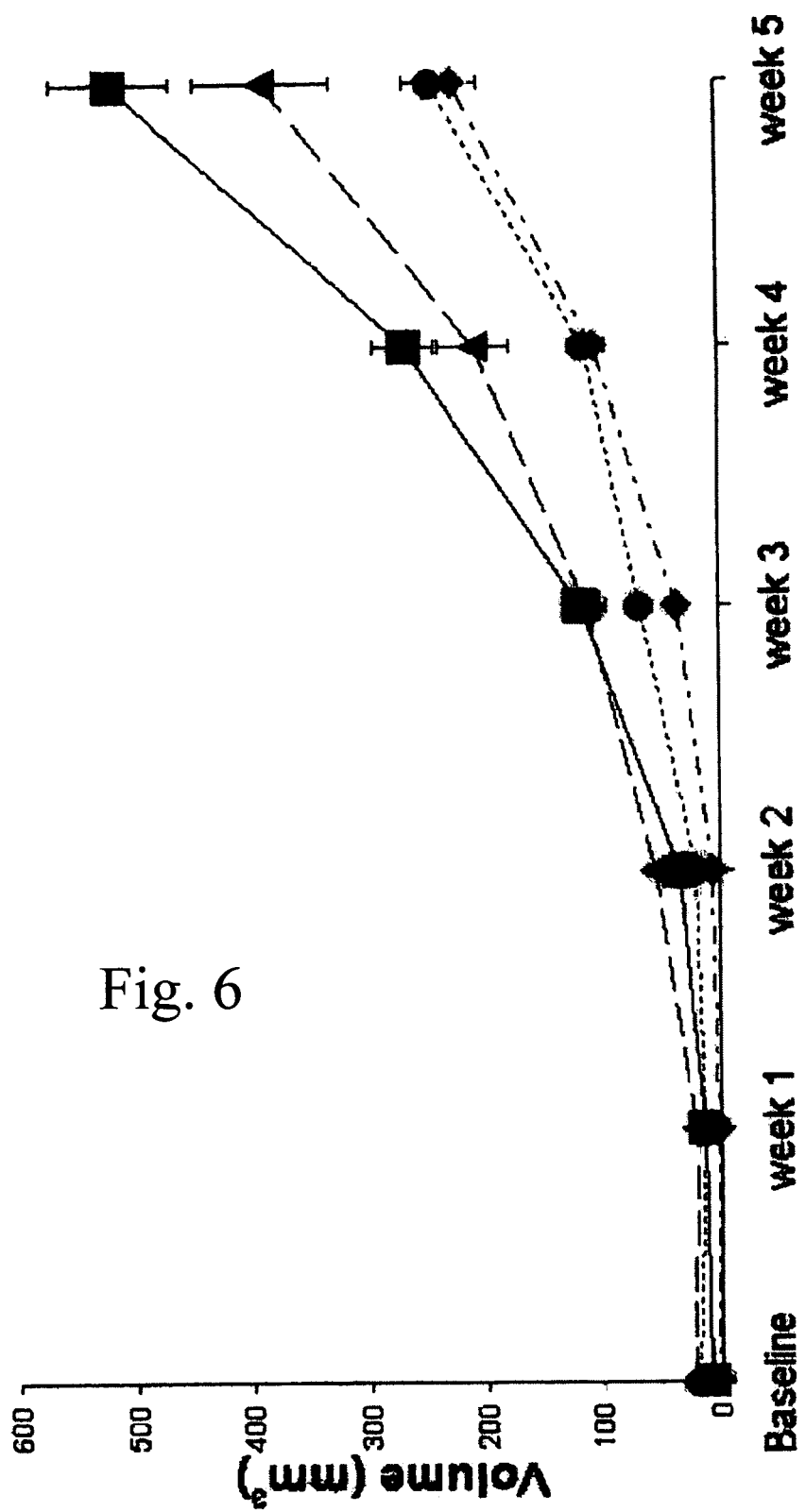
FIG. 6 Decreasing effect of ANP (■), LANP (●), vessel dilator (◆) and kaliuretic peptide (▲) with increasing length of their respective infusions. When each of these peptide hormones were infused for four weeks at their respective 1.4 µg/min/kg of body weight concentrations there was a mean doubling in human pancreatic tumor volume weekly from the second week through the fourth week and in the week after stopping their infusion (week 5) that was significant at P<0.05 when evaluated by ANOVA with a repeated measures design for within group comparisons with Fishers LSD as a post hoc test. United (control) human pancreatic adenocarcinomas are illustrated as ○.

Increase in Tumor Volume after First Week of Respective Peptide Hormone Infusions At the end of the second week of these respective peptide hormone four-week infusions, there were cancers in each of the four peptide hormone-treated groups that had no increase in their tumor volume. The overall trend in each group, however, was an increase in tumor volume approximately 2-fold (FIG. 6). At the same time, the volume of the adenocarcinomas in the placebo-treated animals increased from a 20-fold increase at end of the first week after they became palpable to 69-fold increase in tumor volume at end of the second week after they became palpable. During the third and fourth week of treatment with vessel dilator, LANP, kaliuretic peptide and ANP, a doubling in the volume of tumors occurred in each week (FIG. 6). This doubling in the volume of the tumors continued in the week after the respective infusion ceased, i.e., the end of the fifth week versus the end of the infusions after the fourth week (FIG. 6).

Cyclic GMP Inhibits the Growth of the Adenocarcinomas

With respect to the mechanism of these peptide hormones' tumor growth suppressing effects in vivo, each of these peptide hormones have been shown by the inventor to inhibit DNA synthesis 83% or greater in these human pancreatic adenocarcinoma cells but they do not appear to affect apoptosis. One of the known intracellular messengers of these peptide hormones, i.e., cyclic GMP inhibits DNA synthesis in these cancer cells 51%. The other known mediator of some of these peptide hormones effects, i.e., prostaglandin E2 did not have any significant effect on DNA synthesis in these cancer cells. Since cyclic GMP inhibits DNA synthesis in the human pancreatic adenocarcinomas of this investigation, the cell permeable analog of cyclic GMP i.e., 8-bromo-cyclic GMP was investigated in the present investigation to determine if it could decrease the tumor volume of the human adenocarcinomas in vivo. In the in vitro experiments, 5 mM of cyclic GMP caused the maximal inhibition of DNA synthesis in the human pancreatic adenocarcinoma cells.

Figure 7:
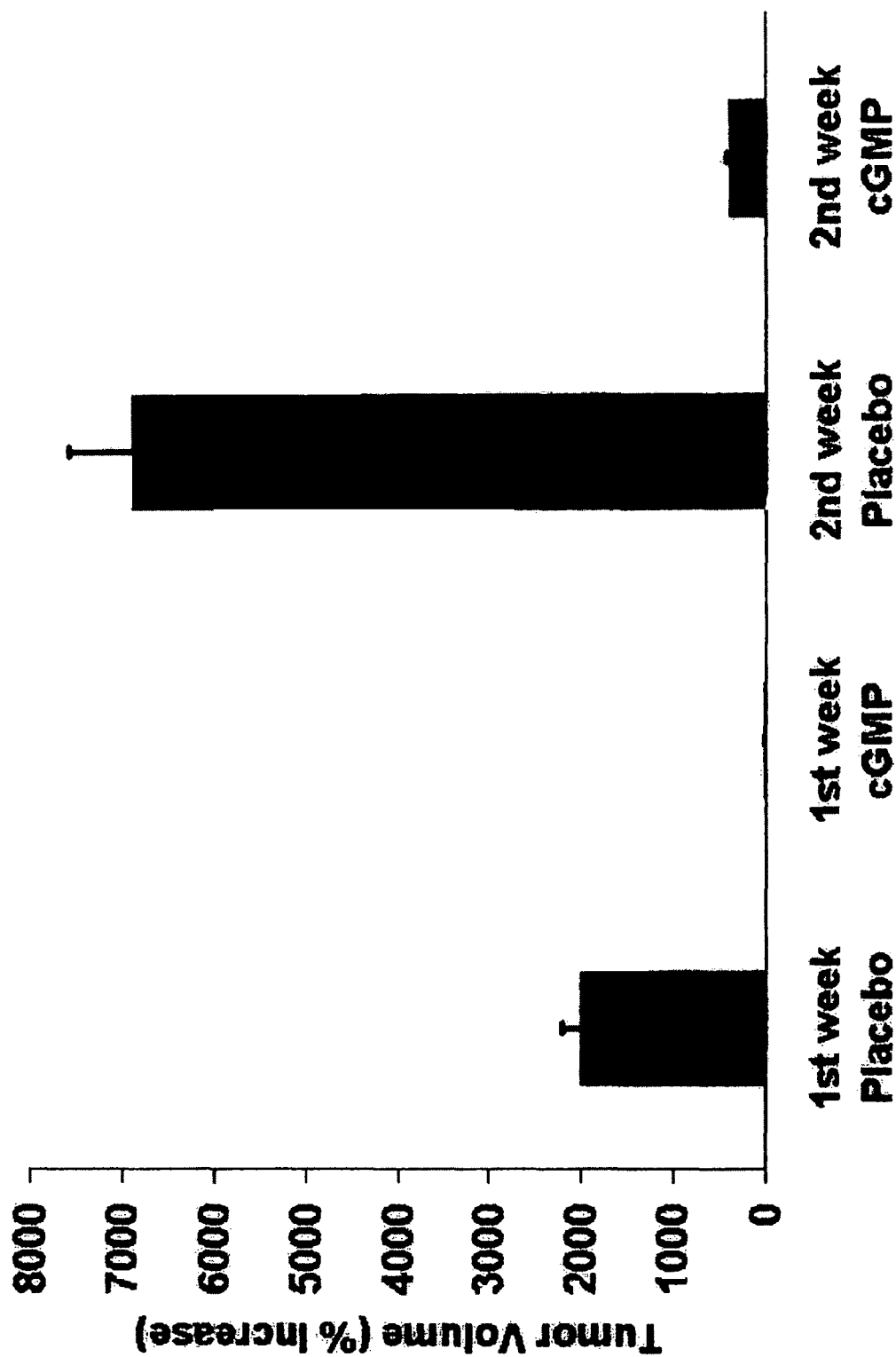
FIG. 7 Cyclic GMP decreases the growth of human pancreatic adenocarcinomas. 8-bromo-cyclic GMP, the cell permeable analog of cyclic GMP, was infused for two weeks at 5 mM/kg body weight/min with only a 0.4 mm$^3$ increase in tumor volume in one week. In the treated animals (versus 35 mm$^3$ increase in tumor volume in placebo treated mice, P<0.01). The 2-fold increase in tumor volume at the end of two weeks with cyclic GMP that was significant (P<0.01) compared to a 69-fold increase in tumor volume of placebo-treated athymic mice with human pancreatic adenocarcinomas when evaluated by a 2 factor ANOVA for between group comparisons.

Thus, 5 mM/min/kg of body weight was chosen as the in fusion dose of cyclic GMP for two weeks. After a one-week infusion of cyclic GMP the volume of the human pancreatic adenocarcinomas cancers increased only 0.4 mm$^3$ (i.e., 9% increase in tumor volume versus 2000% increase in tumor volume in placebo-treated animals, $P<0.01$, n=5 (FIG. 7). After two weeks of cyclic GMP infusion, the volume of the human pancreatic adenocarcinomas was 16.8 mm$^3$ (FIG. 7) i.e., a 3.9-fold increase in volume from baseline versus a 69-fold increase in volume of placebo-treated human adenocarcinomas.

Vessel dilator, long acting natriuretic peptide (LANP) and kaliuretic peptide completely inhibited the growth of human pancreatic adenocarcinomas and decreased their tumor volume during a one-week infusion while there was simultaneously a marked growth (20-fold increase in tumor volume; $P<0.001$) of these adenocarcinomas in the placebo treated athymic mice. Atrial natriuretic peptide (ANP) also had growth inhibiting properties during a one-week infusion but its growth inhibiting property was not as significant as the other three peptide hormones, i.e., there was no decrease in tumor volume with ANP treatment. The ability to inhibit the growth of human pancreatic adenocarcinomas in vivo mimicked the pattern of their growth inhibitory properties in vitro where ANP was also the least potent in decreasing the number of human pancreatic adenocarcinoma cells and the least potent in inhibiting DNA synthesis in these cancer cells. Vessel dilator, LANP, kaliuretic peptide, and ANP, each at 1 µM, decreased the number of human pancreatic adenocarcinoma cells in culture by 65% ($P<0.001$), 47% ($P<0.01$), 37% ($P<0.05$) and 34% ($P<0.05$) respectively, within 24 hours. In the present in vivo investigation a quantitative decrease in cell number within the tumors was not discernable, but after one week the tumor volume decreased by 49%, 28%, and 111% secondary to vessel dilator, long acting natriuretic peptide, and kaliuretic peptide, respectively. During this same time period in the adenocarcinomas treated with ANP their tumor volume increased 109% (versus 2000% increase in volume in placebo treated tumors). Thus, the ability of these cardiovascular hormones to decrease the tumor volume of these cancers in vivo paralleled their ability to decrease the number of cancer cells in vitro with vessel dilator>LANP>kaliuretic peptide>ANP.

When the in vivo experiments with each of the peptide hormones were continued for four weeks, each of the four peptide hormones had a decreased ability to inhibit the growth of these tumors with passage of time. Tumors increased in volume with at least doubling in volume with the passing of each week, i.e., at four weeks of the infusion the tumors had 2-fold or greater increase in volume than at one week and had at least 2-fold larger volume at the end of the third week versus the second week with a similar doubling in volume occurring in the fourth week versus the third week of the infusion (FIG. 6). This doubling in volume of the adenocarcinomas continued in the after the respective infusions ceased, i.e., the end of the fifth week versus the end of the infusions after the fourth week. There are several possible reasons for these findings. First, these peptide hormones were exposed to body temperature for four weeks with the body temperature of these mice ranging from 97.5° F. to 100° F. Heat is well-known to degrade peptide hormones. With being exposed to a temperature of 100° F. for more than a week, it is possible that this temperature degraded these peptide hormones causing them to lose their biologic effects. A second possibility is that these peptide hormones simply being in solution (i.e. 0.9% saline) for more than a week lose their biologic activity. The combination of being in a solution at a temperature of 100° F. for over a week would appear to be a viable possibility for the four week infusion findings of the present investigation. Hormones simply being in solution (i.e., 0.9% saline) for more than a week lose their biologic activity. The combination of being in a solution at a temperature of 100° F. for over a week would appear to be a viable possibility for the four-week infusion findings of the present investigation. A preliminary investigation of human breast carcinomas in athymic mice suggests that these two reasons probably are the cause as when the pumps are changed weekly, the breast cancers disappear after three weeks (Vesely DL, unpublished observation).

A third possibility for these peptide hormones having very potent growth inhibiting effects on adenocarcinomas in vivo for one week and then their effects diminishing with time is that the adenocarcinomas may have mutated to become unresponsive to the peptide hormones. One of the first steps in the mechanism of action of peptide hormones is binding to their specific receptors. The human pancreatic adenocarcinomas of this investigation have ANP receptors present. A mutation of a receptor for a peptide hormone could cause the tissue or cancer with this receptor to no longer respond to the peptide hormone. This would appear to be an unlikely cause of the findings of the present investigation as these four peptide hormones each have separate receptors. Since the response to all four hormones diminished with time, four different mutations would have to occur in one week to mutate four different receptors, which would be highly unlikely. There could, however, be a single post-receptor mutation that could effect the biologic activity of all four peptide hormones since they have a similar mechanism of action mediated by cyclic GMP after binding to their respective receptors. Since cyclic GMP was found in the present investigation to mediate most of these peptide hormones' anticancer effects and these peptide hormones increase the concentration of cyclic GMP by enhancing the activity of the enzyme guanylate cyclase which forms cyclic GMP rather than inhibiting the enzyme(s) which breaks down cyclic GMP, i.e., cyclic GMP phosphodiesterases, the most likely site for a mutation would be in the enzyme guanylate cyclase. If guanylate cyclase became mutated within the adenocarcinomas, these peptide hormones would no longer be able to increase cyclic GMP within the tumor cells and they would lose their anticancer effects. This mutation, however, would have to occur after only one week to explain the findings of the present investigation.

It should be pointed out that there was no cytotoxicity in the present investigation to normal tissues with infusion of these peptide hormones. This is similar to what has been found previously with infusion of these peptide hormones in animals and humans with concentrations similar to that utilized in the present investigation. There has never been any evidence of cytotoxicity or bone marrow suppression with these peptide hormones and/or cyclic GMP. The only known side effect of these peptide hormones is hypotension and this side effect has been seen only with ANP of these four peptide hormones. With infusion of the other three hormones (i.e., vessel dilator, LANP and kaliuretic peptide), which increase cyclic GMP in over 50 healthy humans and in over 50 individuals with congestive heart failure, there has not been a single side effect. Specifically, there has never been an episode of hypotension with infusion of vessel dilator, long acting natriuretic peptide, or kaliuretic peptide in humans or animals. The tumor-bearing athymic mice of the present investigation were energetic and well groomed and did not appear to have any adverse effect from the respective peptide hormone and/or cyclic GMP infusions.

With respect to the mechanism of action of the decrease in tumor volume secondary to vessel dilator, LANP and kaliuretic peptide in the present investigation and the slowing of growth of the human pancreatic adenocarcinomas by all four peptide hormones, it is known that all four of these peptide hormones decrease the number of human pancreatic cancer cells 34% to 65% within 24 hours in vitro mediated by inhibiting DNA synthesis 83% or greater. Vessel dilator, LANP, kaliuretic peptide, and ANP, when incubated with these human pancreatic adenocarcinoma cells each at their 1 μM concentration for 24 hours Inhibit DNA synthesis in these cancer cells by 91%, 84%, 86% and 83%, respectively. These peptides' cancer growth inhibiting mechanism of action appears to be mainly through inhibiting DNA synthesis as they appear to have little effect on enhancing apoptosis, i.e., programmed cell death of adenocarcinomas. This inhibition of DNA synthesis appears mediated in part by the intracellular mediator cyclic GMP as cyclic GMP inhibits DNA synthesis in these adenocarcinoma cells by 51%. In the present investigation cyclic GMP given via osmotic pump markedly decreased the growth of the human pancreatic adenocarcinomas in the first week with only a 9% increase in tumor volume versus a 109% increase with ANP and a 2000% increase in tumor volume in the untreated adenocarcinomas. This knowledge shows that cyclic GMP mediates all of ANP's tumor growth inhibiting effects. This data would further suggest that cyclic GMP mediates the majority of vessel dilator, LANP and kaliuretic peptide's ability to decrease tumor volume and inhibit the growth of adenocarcinomas.

Accordingly, the present investigation shows the utility of these peptide hormones and/or cyclic GMP for treating human pancreatic adenocarcinomas in that three of these peptide hormones completely inhibited the growth of the adenocarcinomas (and decreased their tumor volume) during the first week of their infusion while cyclic GMP inhibited 95% of the pancreatic adenocarcinoma growth. This study shows that these peptide hormones will need to be given weekly rather than continuously for a month to be effective (i.e., the present investigation suggests that one week is the ideal dosing compared to 2, 3, or 4 week continuous infusions of these hormones). Since these peptide hormones anti-tumor effects are mainly through inhibiting DNA synthesis, combining them with agents that mainly enhance apoptosis may be a valuable addition to treating pancreatic adenocarcinomas which now have a median survival of only four months.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of inhibiting the growth of cancer cells in vivo comprising the step of contacting at least one target cancer cell in vivo with an effective amount of 8-bromo-cyclic guanosine monophosphate, or a composition comprising 8-bromo-cyclic-guanosine monophosphate, and further comprising contacting the at least one target cancer cell in vivo with an effective amount of a peptide hormone selected from the group consisting of long acting natriuretic peptide, vessel dilator peptide, and kaliuretic peptide, whereby the in vivo growth of the at least one target cancer cell is inhibited, wherein the target cancer cell is selected from the group consisting of human pancreatic adenocarcinoma, human small-cell carcinoma, and human squamous cell carcinoma.

2. A method of inhibiting the growth of cancer cells in vivo comprising the step of contacting at least one target cancer cell in vivo with an effective amount of 8-bromo-cyclic guanosine monophosphate, or a composition comprising 8-bromo-cyclic-guanosine monophosphate, and further comprising contacting the at least one target cancer cell in vivo with an effective amount of a peptide hormone selected from the group consisting of long acting natriuretic peptide, vessel dilator peptide, and kaliuretic peptide, whereby the in vivo growth of the at least one target cancer cell is inhibited, wherein the target cancer cell is selected from the group consisting of human pancreatic adenocarcinoma, human small-cell carcinoma, and human squamous cell carcinoma, and wherein the contacting step does not comprise contacting the at least one target cancer cell with atrial natriuretic peptide (ANP).

3. The method of claim 1, wherein the peptide hormone is long acting natriuretic peptide.

4. The method of claim 1, wherein the peptide hormone is vessel dilator peptide.

5. The method of claim 1, wherein the peptide hormone is kaliuretic peptide.

6. The method of claim 2, wherein the peptide hormone is long acting natriuretic peptide.

7. The method of claim 2, wherein the peptide hormone is vessel dilator peptide.

8. The method of claim 2, wherein the peptide hormone is kaliuretic peptide.

9. The method of claim 1, wherein the target cancer cell is a human pancreatic adenocarcinoma.

10. The method of claim 2, wherein the target cancer cell is a human pancreatic adenocarcinoma.

11. The method of claim 1, wherein the 8-bromo-cyclic guanosine monophosphate, the peptide hormone, or the composition is provided in a pharmaceutically acceptable carrier.

12. The method of claim 1, wherein the method further comprises contacting the at least one target cancer cell with an effective amount of an agent which has a stimulatory effect on cyclic guanosine monophosphate (cGMP).

13. The method of claim 2, wherein the 8-bromo-cyclic guanosine monophosphate, the peptide hormone, or the composition is provided in a pharmaceutically acceptable carrier.

14. The method of claim 2, wherein the method further comprises contacting the at least one target cancer cell with an effective amount of an agent which has a stimulatory effect on cyclic guanosine monophosphate (cGMP).

15. The method of claim 1, wherein the target cancer cell is a human small-cell carcinoma.

16. The method of claim 1, wherein the target cancer cell is a human squamous cell carcinoma.

17. The method of claim 2, wherein the target cancer cell is a human small-cell carcinoma.

18. The method of claim 2, wherein the target cancer cell is a human squamous cell carcinoma.

* * * * *

UNITED STATES PATENT AND TRADEMARK OFFICE
CERTIFICATE OF CORRECTION

PATENT NO.       : 8,759,317 B2                                              Page 1 of 1
APPLICATION NO.  : 11/162056
DATED            : June 24, 2014
INVENTOR(S)      : David L. Vesely It is certified that error appears in the above-identified patent and that said Letters Patent is hereby corrected as shown below:

In the Specification

Column 12,
Line 34, "and 111%" should read --and 11%--

Signed and Sealed this
Twenty-first Day of April, 2015

Michelle K. Lee
*Director of the United States Patent and Trademark Office*